(12) United States Patent
Hao et al.

(10) Patent No.: US 10,752,963 B2
(45) Date of Patent: Aug. 25, 2020

(54) MICRO-FLUIDIC CHIP AND ITS MODIFICATION METHOD AND APPLICATION IN DETECTION OF THE QUANTITY OF FOOD BACTERIA

(71) Applicant: GREENTOWN AGRICULTURAL TESTING TECHNOLOGY CO., LTD, Hangzhou, Zhejiang Province (CN)

(72) Inventors: Xingkai Hao, Hangzhou (CN); Yuqian Jiang, Ottawa (CA); Xudong Cao, Ottawa (CA); Chuanpi Wang, Hangzhou (CN); Min Zhou, Hangzhou (CN); Meina Sun, Hangzhou (CN); Zhen Wang, Hangzhou (CN)

(73) Assignee: GREENTOWN AGRICULTURAL TESTING TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 16/044,452

(22) Filed: Jul. 24, 2018

(65) Prior Publication Data
US 2019/0323064 A1 Oct. 24, 2019

(30) Foreign Application Priority Data
Apr. 24, 2018 (CN) .......................... 2018 1 0370194

(51) Int. Cl.
*C12Q 1/689* (2018.01)
*B01L 3/00* (2006.01)

(52) U.S. Cl.
CPC ........ *C12Q 1/689* (2013.01); *B01L 3/502707* (2013.01); *B01L 2300/0636* (2013.01); *B01L 2300/123* (2013.01); *C12Q 2600/142* (2013.01)

(58) Field of Classification Search
CPC ............. C12Q 1/689; C12Q 2600/142; B01L 3/502707; B01L 2300/0636; B01L 2300/123
See application file for complete search history.

(56) References Cited

U.S. PATENT DOCUMENTS

| | | | |
|---|---|---|---|
| 2005/0003361 A1* | 1/2005 | Fredriksson | C12Q 1/6876 435/5 |
| 2007/0099351 A1* | 5/2007 | Peters | G01N 27/4146 438/142 |

(Continued)

OTHER PUBLICATIONS

Guo et al. Anal Bioanal Chem. 2016. 408:4715-4722 (Year: 2016).*

*Primary Examiner* — Joseph G. Dauner
(74) *Attorney, Agent, or Firm* — Jiwen Chen; Jacobson Holman PLLC (57) ABSTRACT

A micro-fluidic chip and its modification method and application in detection of food bacteria quality, includes the following steps: changing a functional group —$CH_3$ on the internal surface of micro-fluidic channel of micro-fluidic chip to a functional group —OH through modification; Supplying amino silane reagent to the micro-fluidic channel; supplying dendritic polymer as modified by —COOH to internal surface of the micro-fluidic channel after drying; grafting primer of aminated aptamer RCA on terminus 5' and hybrid from its padlock probe on dendrimer on internal surface of the micro-fluidic channel; wherein, the padlock probe is the complementary sequence of the aptamer of the target pathogenic bacteria to be tested; after that, supplying RCA reaction reagent to the micro-fluidic channel to make aptamer RCA generate long-chain aptamer in series. The present invention adopts two RCA reactions of varied functions in combination, and uses dendritic polymer to modify internal surface of the chip.

5 Claims, 4 Drawing Sheets

Specification includes a Sequence Listing.

(56) References Cited

U.S. PATENT DOCUMENTS

| | | | |
|---|---|---|---|
| 2009/0275130 A1* | 11/2009 | Navran | C12N 15/1048 435/366 |
| 2010/0003678 A1* | 1/2010 | Dittmer | G01N 33/54346 435/6.11 |
| 2010/0317128 A1* | 12/2010 | Harada | C12Q 1/6816 436/501 |
| 2012/0129157 A1* | 5/2012 | Barnhizer | C12Q 1/04 435/5 |
| 2013/0040837 A1* | 2/2013 | Karp | C12N 15/115 506/9 |
| 2013/0183658 A1* | 7/2013 | Barnhizer | G01N 33/54366 435/5 |
| 2014/0378339 A1* | 12/2014 | Lammertyn | B01L 3/502707 506/9 |
| 2017/0240889 A1* | 8/2017 | Lee | C12N 15/113 |

* cited by examiner

MICRO-FLUIDIC CHIP AND ITS MODIFICATION METHOD AND APPLICATION IN DETECTION OF THE QUANTITY OF FOOD BACTERIA

This application claims the priority benefit of Chinese Application No. 201810370194.2, filed Apr. 24, 2018 in Chinese, which is hereby incorporated by reference.

FIELD OF THE INVENTION

The present invention is related to the technical field of food detection and measurement, in particular to a micro-fluidic chip and its modification method and application in detection of the quantity of food bacteria.

BACKGROUND ARTS

Foodborne diseases have attracted great attentions as food safety is one of the major concerns to public health. Therefore, quick and sensitive detection equipments are extremely essential for food hygiene inspection. Similarly, for food processing enterprises and food supervision departments, quick detection of the quantity of target bacteria in the food is favorable for improvement of monitoring of food quality and effective public food hygiene and safety protection.

Presently, conventional methods for detection of foodborne pathogens include biochemical identification, Enzyme-Linked Immunosorbent Assay (ELISA), PCR and so on. However, such methods have certain disadvantages, such as complicated preliminary processing of samples and extraction of DNA, long detection cycle, low detection sensibility and the lack of economical, convenient, quick and sensitive detection techniques. On the contrary, biosensor technology based on micro-fluidic chip has become a R&D focus owing to such advantages as high flux, miniaturization, automation and easy integration.

As micro-fluidic chip can integrate complicated chemical processes into a chip, numerous quick detection equipment based on micro-fluidic chip have appeared in recent years, such as electrochemical micro-fluidic chip, impedance micro-fluidic chip and so on. According to their detection principles, most of such chips aim to detect the quantity of bacteria through measurement of variation to the current or resistance of micro-fluidic equipments before and after the detection of target bacteria. The advantage of such equipment lies in the fact that it can analyze extremely low quantity of bacteria. However, such equipment is not easy for operation and is relatively expensive.

Another type of equipment taking the micro-fluid as the basis for detection is based on optic detection principles (fluorescent staining or color variation). The advantage of such detection mechanism lies in the fact that detection signal can be directly observed and detected to realize quantification of target bacteria. Despite of its relatively low price, such method has higher requirements for superficial modification of micro-fluidic materials in view of reducing noise signals produced by other non-target particles in food samples and interference to the detection signals.

Rolling circle amplification (RCA) is based on signal amplification technology on nucleic acid amplification, which has been used for detection of cells, proteins, and other small molecules. According to its working principles, it takes circular DNA as the template to convert deoxynucleotide (dNTPs) into single-stranded DNA products under the catalysis of DNA polymerase by using a primer complementary to both ends of the padlock probe (it can form a circular template). RCA products comprise hundreds or thousands of tandem repeated DNA fragments complementary to the template. As one of isothermal nucleic acids amplification techniques, RCA features in high reaction efficiency, moderate conditions and low operation cost of instruments as compared with Polymerase Chain Reaction (PCR). RCA is applied to signal amplification during detection of foodborne pathogens to effectively enhance detection signals. Objectively, detection sensitivity of such technology requires enhancement through improvement of identification and capture of targets.

With regard technologies on gene chips, aptamers are frequently used to identify and capture targets for detection. As compared with antibodies, aptamers as obtained through screening are available for in-vitro synthesis in large quantity, which features in excellent repeatability, high stability, easy storage and low cost. Activities of aptamers are not to be affected when used in combination with labelled fluorescence. Furthermore, the aptamers have extensive targets, including pesticides, tissues, cells, viruses, proteins, toxins, vitamins, allergens and so on. They are normally applied to aptamers of micro-fluidic chips, which are connected to the detection area in a single layer. However, such aptamers are unfavorable for contact with and identification of such large targets as bacteria cells due to their limited volume. Furthermore, their capture efficiency is also low.

SUMMARY OF THE INVENTION

To solve aforesaid problems, the present invention provides a micro-fluidic chip modification method. The present invention makes use of RCA technology to realize in-situ production of a long-chain series aptamers on the internal surface of the micro-fluidic to modify existing micro-fluidic chip, and prepare a micro-fluidic chip that is available for quick detection of the quantity of food bacteria.

Technical solution of the present invention provides a micro-fluidic chip modification method, comprising the following steps:
(1) changing a functional group —$CH_3$ on the internal surface of micro-fluidic channel of micro-fluidic chip to a functional group —OH through modification;
(2) supplying an amino silane reagent to the micro-fluidic channel for amino silane reaction once the reaction in Step (1) is completed;
(3) after drying, supplying a dendritic polymer as modified by —COOH to an internal surface of the micro-fluidic channel for coupled reaction;
(4) once the reaction in Step (3) is completed, grafting a primer of aminated aptamer RCA on terminus 5' and hybrids from its padlock probe on the dendritic polymer on the internal surface of the micro-fluidic channel; wherein, the padlock probe is the complementary sequence of the aptamer of the target pathogenic bacteria to be tested; after that, supplying RCA reaction reagent to the micro-fluidic channel to make aptamer RCA generate long-chain aptamer in series; terminating RCA reaction through heating upon completion of reaction; finally, supplying phosphate buffer to the micro-fluidic channel for cleaning.

According to the present invention, modification to the internal surface of the micro-fluidic chip by the dendritic polymer has provided a mass of binding sites for RCA, and has reduced non-specific adsorption of impurities in detection samples. The sequence of RCA products in the present invention is determined by the template. Therefore, it is applicable to obtain RCA product containing target sequence through editing template sequence. It is also applicable to produce series aptamers by taking complementary sequence of aptamers of targets as the sequence of cyclic template of RCA. Such RCA reaction that can produce series aptamers can facilitate in-situ synthesis of long-chain aptamers on the micro-fluidic chip. This aims to realize significant increase in captured aptamers as distributed in terms of quantity and space, improve efficiency in capturing target pathogens, and accomplish comprehensive detection. On this account, the present invention can significantly improve efficiency in capturing target cells without extraction of such large-molecule substances as DNAs or proteins.

According to the present invention, there are numerous dendritic polymers for selection. In a preferred embodiment, the dendritic polymer in Step (3) is polyethylenediamine dendritic polymer.

As a preferred embodiment, Step (4) comprises the following steps:

(4-1) Taking 50 µl reaction system as an instance, heating 2 µM primer for aptamer RCA and 2 µM padlock probe under the temperature of 95° C. for 5 minutes before cooling down to the room temperature; place it into 37° C. water bath, and wait for 30 min before adding 10 U T4 DNA ligase and 5 µl 10×T4 DNA ligase buffer for reaction under the room temperature for 30 min; after that, heat it to the temperature of 65° C., and maintain the temperature for 10 min before terminating the reaction to obtain primer of aptamer RCA and hybrids of its padlock probe;

(4-2) Once the hybrid is grafted on the internal surface of the micro-fluidic channel through carboxyl condensation reaction, supplying the RCA reagent. Taking 100 µl reaction system for instance, the RCA reagent comprises 10 U phi29 DNA polymerase, 10 µl phi29 DNA polymerase buffer and 4 µl dNTPs (10 mM); following reaction under the temperature of 37° C. for 10 hours, maintaining the whole reaction system for 10 min under the temperature of 65° C. before terminating the reaction.

In a preferred embodiment, the primer of the aptamer RCA has the following sequence: SEQ ID NO. 1.

In a preferred embodiment, padlock probe of the primer of the aptamer RCA has the following sequence: SEQ ID NO. 2.

The present invention also provides a micro-fluidic chip obtained through modification with aforesaid method.

The present invention further provides an application method of aforesaid micro-fluidic chip in detection of the quantity of food bacteria As a preferred embodiment, the method comprising the following steps:

(1) Supplying the sample solution to be tested into the micro-fluidic channel; once internal surface of micro-fluidic channel on the micro-fluidic chip as modified by the target pathogenic bacteria in the sample solution to be tested is identified and captured, supplying aptamer of Signal amplified RCA-primer compound and padlock probe into the micro-fluidic channel for identification and specific adsorption on the surface of target pathogenic bacteria;

(2) Putting the fluorescent probe subjecting to specific identification with Signal amplified RCA into the micro-fluidic channel; following reaction excitation, Signal amplified RCA will produce a binding site for fluorescent probe;

(3) Observing reaction area of the micro-fluidic chip under the fluorescent microscope, and taking photos; using photo processing software to convert the fluorescent photos into quantitative fluorescent signals; comparing the detection signals with standard curve to realize quantitative detection of foodborne pathogens.

The present invention has designed a RCA reaction that can produce aptamers with specific sequence; furthermore. The present invention t can integrate aptamers with signal amplified RCA and dendritic polymer to realize "triple" effect in bacteria detection, and improve the following detection effects:

(1) Modification to an internal surface of the micro-fluidic chip by the dendritic polymer has provided a mass of binding sites for the RCA, and has reduced non-specific adsorption of impurities in detection samples.

(2) Aptamer RCA can produce a mass of repeated series long-chain aptamers to realize significant increase in captured aptamers as distributed in terms of quantity and space, and improve efficiency in capturing targets.

(3) Signal amplified RCA converts targets as identified and captured into fluorescent signals to further improve the detection sensibility.

In a preferred embodiment, aptamer-primer compound of the Signal amplified RCA has the following sequence: SEQ ID NO. 3;

The padlock probe corresponding to aptamer-primer of the signal amplified RCA has the following sequence: SEQ ID NO. 4.

In a preferred embodiment, the fluorescent probe has the following sequence: SEQ ID NO. 5.

As compared with existing arts, the present invention has the following beneficial effects:

(1) The present invention makes use of RCA sequence for in-situ production of long-chain series aptamers inside the micro-fluidic chip so as to ensure doubled and redoubled increase in the quantity of aptamers, and improve efficiency in capturing target bacteria. Furthermore, significant increase in the length of aptamers has further increased contact area between aptamers and target bacteria cells. This is favorable for improvement of identification and capture efficiency as well as enhancement of detection sensibility.

(2) According to the present invention, reaction of aptamer RCA can realize in-situ production of aptamers for direct use, which can simplify modification steps, and reduce detection cost.

(3) The present invention adopts two RCA reactions of varied functions in combination, and uses a dendritic polymer to modify the internal surface of the chip so as to improve identification and capture of targets and signal enhancement, and realize integrated detection.

PREFERRED EMBODIMENTS OF THE INVENTION

Embodiment 1

Part 1: Modification to Internal Surface of Micro-Fluidic Chip

Figure 2:
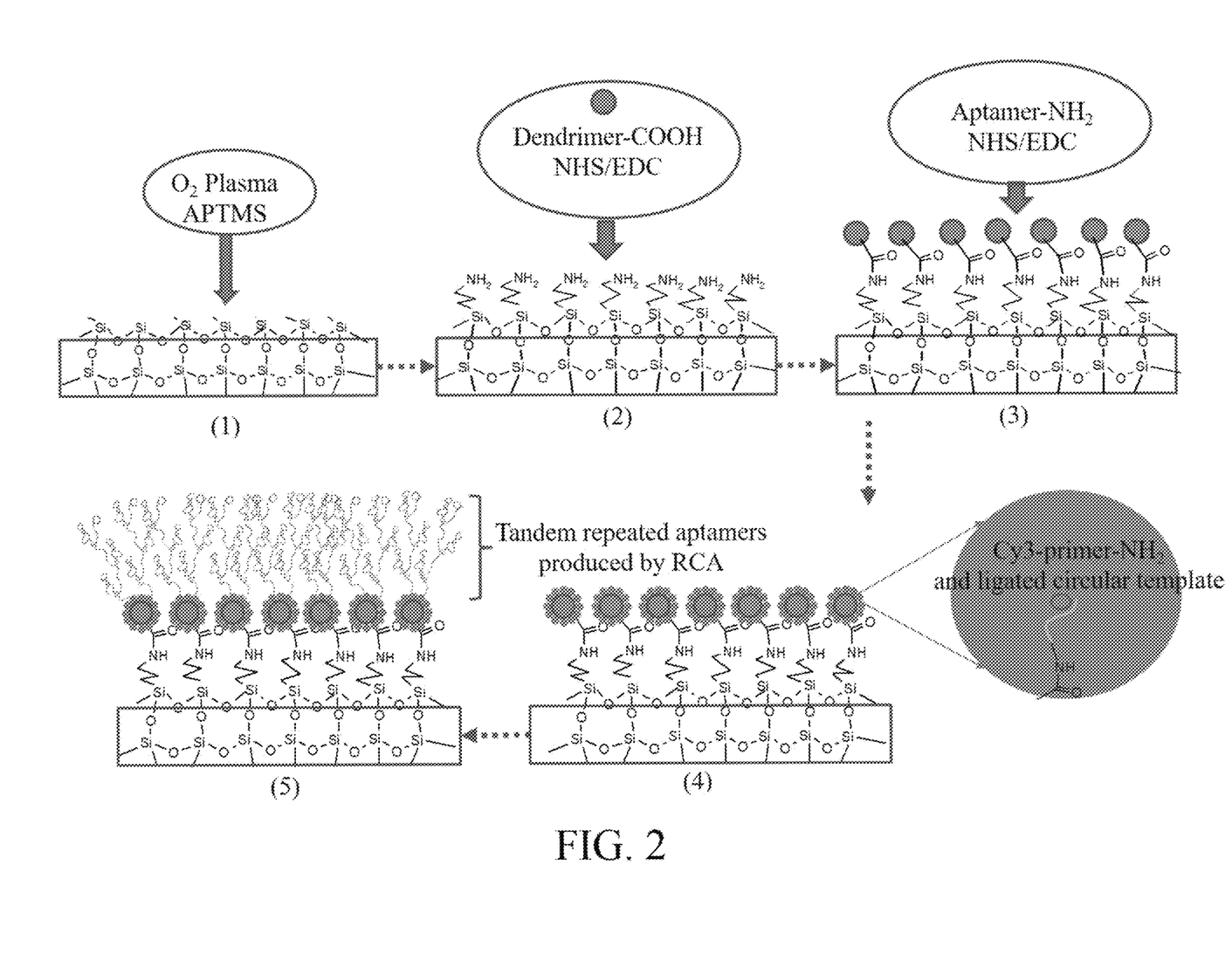
FIG. 2 is the diagram showing modification process on the internal surface of bacteria detection micro-fluidic chip and production of series aptamers by aptamer RCA according to the present invention.
Figure 3:
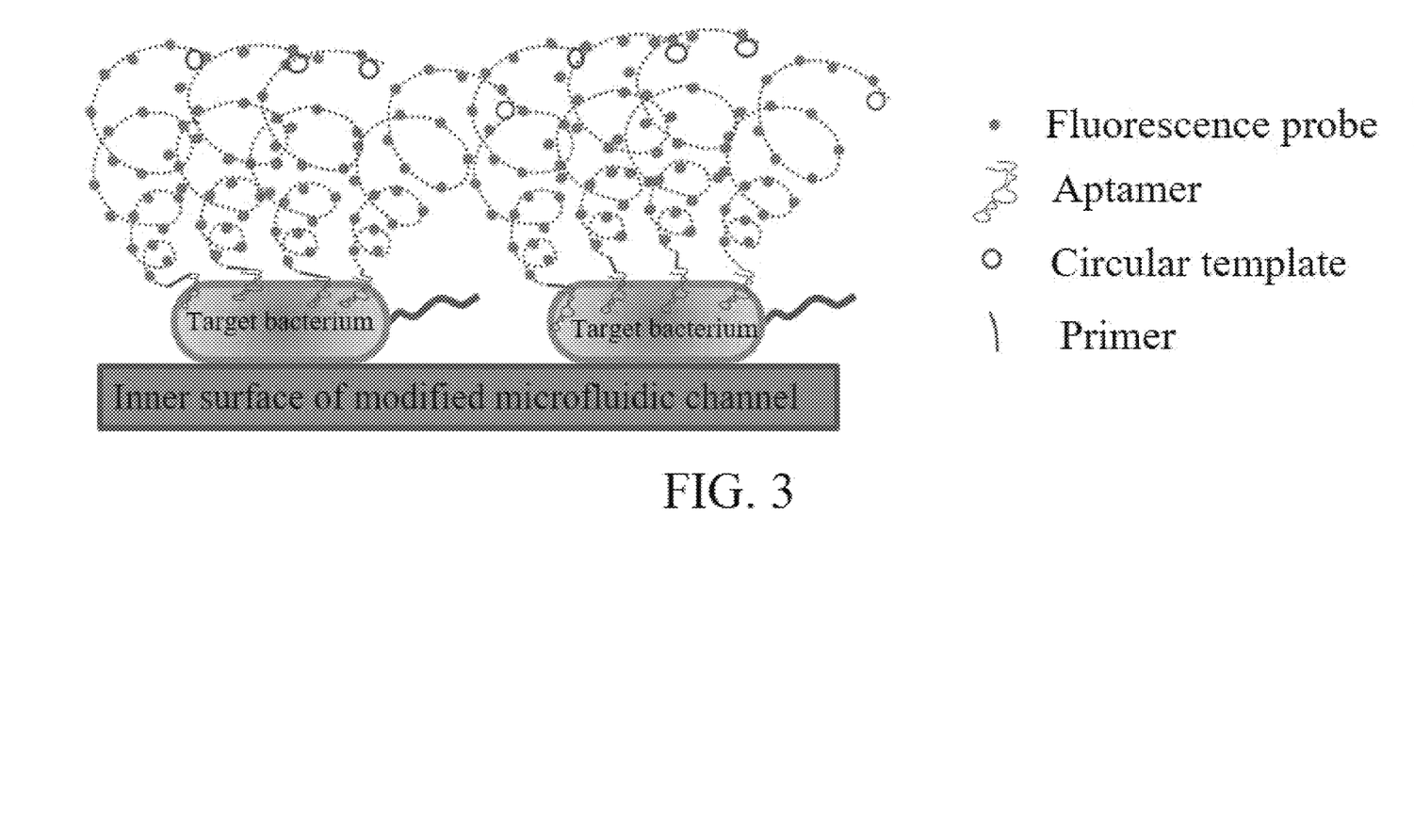
FIG. 3 is the schematic diagram for RCA signal amplification according to the present invention.
Figure 4:
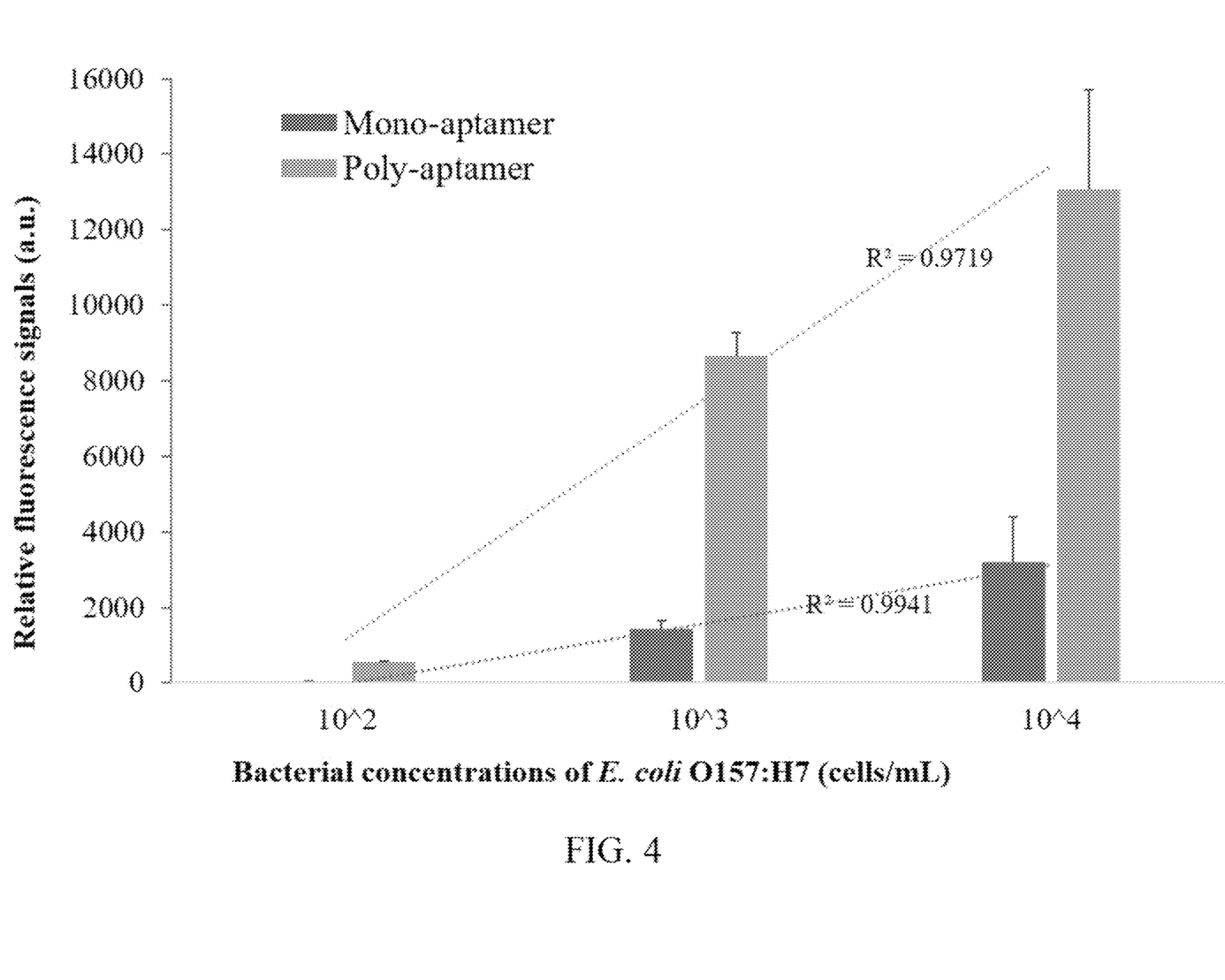
FIG. 4 is the comparison diagram for double-layer RCA used to micro-fluidic chip and existing micro-fluidic chip used for detection of fluorescent signal strength of E. coli O157:H7 according to the present invention.

Firstly, a polyethylenediamine dendritic polymer (Generation 7) subjected to superficial carboxylation was grafted on an internal surface of micro-fluidic channel through plasma treatment. The micro-fluidic channel was made of polydimethylsiloxane (PDMS), subjecting to amination by using (3-aminopropyl)-trimethoxysilane (APTMS). This process refers to condensation reaction of carboxyl (FIG. 2, Step 1-3, grafting of dendritic polymer). Existing method as used to this process is not to be described herein in details.

After that, a primer (primer 1) of animated aptamer RCA on terminal 5' and hybrid product from primer 1's padlock probe (padlock probe 1) were grafted on dendritic polymer on the internal surface of the micro-fluidic chip, and a RCA reagent was supplied; aptamer RCA reaction was started to produce series long-chain aptamers, and RCA reaction was terminated through heating once upon completion of reaction. Phosphate buffer was used to clean the channel inside the modified micro-fluidic chip for further use (FIG. 2, Step 4-5, in-situ production of series aptamer product).

The reaction conditions for aforesaid aptamer RCA are as follows:

(1) Taking 50 µl reaction system as an example, heating primer (2 µM) of aptamer RCA and padlock probe (2 µM) under the temperature of 95° C. for 5 minutes before cooling down to the room temperature; placing it into 37° C. water bath, and waiting for 30 min before adding 10 U T4 DNA ligase and 5 µl 10×T4 DNA ligase buffer for reaction under the room temperature for 30 min; after that, heating it to the temperature of 65° C., and maintaining the temperature for 10 min before terminating the reaction. This process primer and padlock probe formed a cyclic template through hybridization.

(2) Once aforesaid linked product is grafted on the internal surface of the micro-fluidic channel, supplying RCA reagent. Taking the 100 µl reaction system for instance, RCA reagent comprises 10 U phi29 DNA polymerase, 10 µl phi29 DNA polymerase buffer and 4 µl dNTPs (10 mM). Following reaction under the temperature of 37° C. for 10 hours, maintaining the whole reaction system for 10 min under the temperature of 65° C. before terminating the reaction.

Part 2: Target Identification and Amplification of Detection Signal

Once the internal surface of the micro-fluidic chip as modified by target pathogens is identified and captured, supplying RCA reagent to the micro-fluid to initiate RCA reaction so as to generate further amplified signals of long-chain RCA product. Once reaction is completed, proceed with heating to the temperature of 65° C., and maintain it for 10 min before terminating RCA reaction.

Reaction conditions for signal amplified RCA are as follows:

(1) Taking 50 µl as an instance, the heat primer compound (200 nM) of aptamer Signal amplified RCA and padlock probe (200 nM) were heated under the temperature of 95° C. for 5 minutes before cooling down to the room temperature; it was placed into 37° C. water bath, and waited for 30 min before adding 10 U T4 DNA ligase and 5 µl 10×T4 DNA ligase buffer for reaction under the room temperature for 30 min; after that, it was heated to the temperature of 65° C., and the temperature was maintained for 10 min before terminating the reaction. This process primer and padlock probe formed a cyclic template through hybridization.

(2) Once the aforesaid link product was delivered into the micro-fluidic chip, and identified and fixed to the surface of target pathogens to be tested, RCA reagent was supplied. Taking a 100 µl reaction system for instance, RCA reagent comprises 10 U phi29 DNA polymerase, 10 µl phi29 DNA polymerase buffer and 4 µl dNTPs (0 mM). Let the whole reaction system subject to reaction under the temperature of 37° C. for 2 hours before termination (65° C., 10 min).

Finally, to identify detection signal, the fluorescent probe subjecting to specific identification with RCA product was inserted into the micro-fluid channel for hybrid with signal amplified RCA product; meanwhile, phosphate buffer was sued to rinse surplus fluorescent probe not bound inside the channel.

Part 3: Collection and Processing of Fluorescent Signal

The reaction area of the micro-fluidic chip was observed under the fluorescent microscope, and photos were taken; photo processing software was used to convert the fluorescent photos into quantitative fluorescent signals. The detection signals were compared with standard curve to realize quantitative detection of foodborne pathogens.

Aforesaid aptamer RCA, primer of signal amplified RCA and corresponding padlock probe are listed in Table 1.

TABLE 1

The Case of Double-Layer RCA Used for Detection of *E. coli* O157:H7 by Micro-fluidic Chip

| | Designation | Sequence (5'-3') |
|---|---|---|
| Aptamer RCA | Primer | 5'-NH$_2$-TTTTT TTTTT GAAGG ACTTA GTTAC TGTCG AGCGA T-3' |
| | Padlock probe | 5'-AACTA AGTCC TTCAT ACGGG AGCCA ACACC ATCTT GTACA AATCG TCTTG ATATC TGCAC ATTTG ATAGA GCAGG TGTGA CGGAT ATCGC TCGAC AGT-3' |
| Signal amplified RCA | Aptamer-primer compound | 5'-NH$_2$-ATCCG TCACA CCTGC TCTAT CAAAT GTGCA GATAT CAAGA CGATT TGTAC AAGAT GGTGT TGGCT CCCGT ATTTT TTTTT GTCCG TGCTA GAAGG AAACA GTTAC-3' |
| | Padlock probe | 5'-TAGCA CGGAC ATATA TGATG GACCG CAGTA TGAGT ATCTC CTATC ACTAC TAAGT GGAAG AAATG TAACT GTTTC CTTC-3' |
| | Fluorescent probe | 5'-Cy3-TTTTA GTATG AGTAT CTC-3' |

Figure 1:
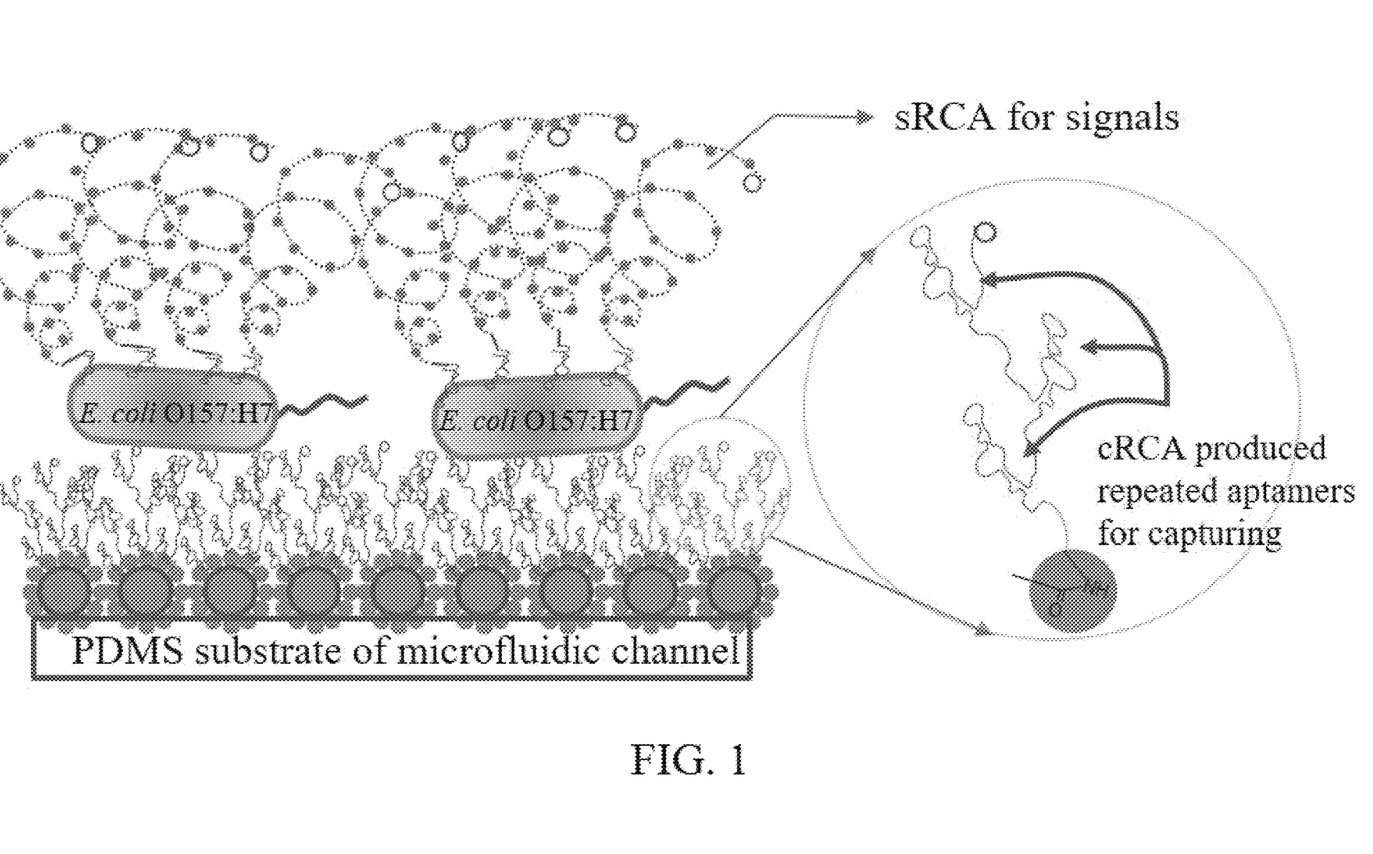
FIG. 1 is the diagram for working principles of the present invention.

Detection principles in this embodiment are as shown in FIG. 1 from the bottom to the top: The first step was the modification to the internal surface of micro-fluidic chip; grafting dendritic polymer (its major functions include provision of a mass of DNA sequence binding sites and reduction of background signals) on the internal surface of the micro-fluidic chip; after that, linking it with the primer of aptamer RCA and cyclic template on the basis of dendritic polymer so as to produce long-chain series aptamers through RCA reaction to improve efficiency in identification and capture of targets. Once target cells are identified and captured, aptamer of signal amplified RCA-primer compound and cyclic template were delivered, identified and adsorbed to the surface of target cells. A mass of fluorescent probe binding sites were produced through RCA reaction to facilitate integration of fluorescent probes through hybridization for the purpose of signal amplification.

The invention claimed is:

1. A method of modifying a micro-fluidic channel of a micro-fluidic chip, the method comprising the following steps:

(1) modifying a —$CH_3$ functional group on an internal surface of the micro-fluidic channel to a —OH functional group;

SEQUENCE LISTING

```
<160> NUMBER OF SEQ ID NOS: 5

<210> SEQ ID NO 1
<211> LENGTH: 36
<212> TYPE: DNA
<213> ORGANISM: Artificial Sequence
<220> FEATURE:
<223> OTHER INFORMATION: Synthesized

<400> SEQUENCE: 1
tttttttttt gaaggactta gttactgtcg agcgat                              36

<210> SEQ ID NO 2
<211> LENGTH: 98
<212> TYPE: DNA
<213> ORGANISM: Artificial Sequence
<220> FEATURE:
<223> OTHER INFORMATION: Synthesized

<400> SEQUENCE: 2
aactaagtcc ttcatacggg agccaacacc atcttgtaca aatcgtcttg atatctgcac    60
atttgataga gcaggtgtga cggatatcgc tcgacagt                           98

<210> SEQ ID NO 3
<211> LENGTH: 105
<212> TYPE: DNA
<213> ORGANISM: Artificial Sequence
<220> FEATURE:
<223> OTHER INFORMATION: Synthesized

<400> SEQUENCE: 3
atccgtcaca cctgctctat caaatgtgca gatatcaaga cgatttgtac aagatggtgt    60
tggctcccgt atttttttttt gtccgtgcta gaaggaaaca gttac                  105

<210> SEQ ID NO 4
<211> LENGTH: 79
<212> TYPE: DNA
<213> ORGANISM: Artificial Sequence
<220> FEATURE:
<223> OTHER INFORMATION: Synthesized

<400> SEQUENCE: 4
tagcacggac atatatgatg gaccgcagta tgagtatctc ctatcactac taagtggaag    60
aaatgtaact gtttccttc                                                79

<210> SEQ ID NO 5
<211> LENGTH: 18
<212> TYPE: DNA
<213> ORGANISM: Artificial Sequence
<220> FEATURE:
<223> OTHER INFORMATION: Synthesized

<400> SEQUENCE: 5
ttttagtatg agtatctc                                                 18
```

(2) performing an amino silane reaction by supplying an amino silane reagent to the micro-fluidic channel after the modifying of step (1) is completed;
(3) drying the micro-fluidic channel after performing step (2);
(4) supplying a —COOH modified dendritic polymer to the micro-fluidic channel for coupled reaction after drying the micro-fluidic channel;
(5) after completing step (4), grafting to the —COOH modified dendritic polymer:
  a primer for producing an aptamer RCA animated on the 5' terminus of the aptamer RCA, and
  a hybrid of a padlock probe comprising a sequence that is complementary to the aptamer RCA;
(6) supplying a RCA reaction reagent to the micro-fluidic channel after the grafting of step (5);
(7) performing an RCA reaction in the micro-fluidic channel to make an aptamer RCA comprising a long-chain of aptamers in series,
  wherein the aptamers target a pathogenic bacteria to be tested;
(8) terminating the RCA reaction through heating once the RCA reaction is completed; and
(9) cleaning the micro-fluidic channel by supplying phosphate buffer to the micro-fluidic channel.

2. The method of claim 1, wherein the —COOH modified dendritic polymer comprises a polyethylenediamine dendritic polymer.

3. The method of claim 1, wherein the RCA reaction agent is supplied in a volume of 100 µl, wherein the volume comprises 10 U phi29 DNA polymerase, 10 µl phi29 DNA polymerase buffer and 10 mM dNTPs;
wherein step (5) comprises the following steps:
  (a) heating 2 µM of the primer and 2 µM of the padlock probe at a temperature of 95° C. for 5 minutes and cooling down to room temperature,
    wherein the heating is performed in a 50 µl reaction system;
  (b) placing the reaction system in a 37° C. water bath for 30 minutes;
  (c) after the 30 minutes, adding 10 U of T4 DNA ligase and 5 µl of 10× T4 DNA ligase buffer to the reaction system;
  (d) performing a ligation reaction at room temperature for 30 minutes;
  (e) heating the reaction system to a temperature of 65° C. and maintaining that temperature for 10 minutes; and
  (f) obtaining the primer and a hybrid of the padlock probe by terminating the ligation reaction; and
wherein step (7) comprises the following steps:
  (a) performing the RCA reaction for 10 hours at a temperature of 37° C.; and
  (b) maintaining for 10 minutes the whole RCA reaction at a temperature of 65° C. before terminating reaction.

4. The method of claim 1, wherein the primer comprises the sequence of SEQ ID NO: 1.

5. The method of claim 4, wherein the padlock probe comprises the sequence of SEQ ID NO: 2.

* * * * *